United States Patent [19]
Ozaki

[11] Patent Number: 5,565,471
[45] Date of Patent: Oct. 15, 1996

[54] METHOD FOR INHIBITING THROMBOSIS

[75] Inventor: Keiko Ozaki, Ibaraki-ken, Japan

[73] Assignee: Mitsubishi Chemical Corporation, Tokyo, Japan

[21] Appl. No.: 186,018

[22] Filed: Jan. 25, 1994

[30] Foreign Application Priority Data

Jan. 25, 1993 [JP] Japan .................... 5-010063

[51] Int. Cl.$^6$ .................................. A61K 31/47
[52] U.S. Cl. ........................................ 514/312
[58] Field of Search ............................. 514/312

[56] References Cited

U.S. PATENT DOCUMENTS 4,258,192  3/1981  Okamoto et al. ............... 546/166

FOREIGN PATENT DOCUMENTS 0008746  3/1980  European Pat. Off. .
0301970  2/1989  European Pat. Off. .
0565897  10/1993  European Pat. Off. .

OTHER PUBLICATIONS

Remington's Pharmaceutical Sciences, 16th edition (1980) pp. 1453–1457.
Mitsubishi Kasei, Database WP1, Week 9026, Derwent Publications Ltd., London, AN90-196839(26) JP-A-92 128 123 (1990).

*Primary Examiner*—Raymond Henley III
*Attorney, Agent, or Firm*—Wenderoth, Lind & Ponack

[57] ABSTRACT

A method for inhibiting the formation of a thrombis is disclosed wherein an antithrombin composition is topically administered in the form of an emulsion which comprises, together with a solvent, a diluent, and an emulsifier, $N^2$-arylsulfonyl-L-arginineamide represented by the general formula (I):

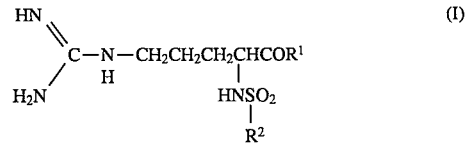

wherein $R^1$ represents (2R,4R)-4-alkyl-2-carboxypiperidino group, $R^2$ represents phenyl group or a condensed polycyclic compound residue as defined below, and said $R^2$ optionally has one or more substituents selected from lower alkyl group, lower alkoxy group or amino group substituted by lower alkyl group, said condensed polycyclic compound residue being a condensed polycyclic compound residue including a benzene ring, said benzene ring being bound to the sulfur atom of the sulfonyl group in the general formula (I) and said benzene ring being condensed with other ring which may be a heterocyclic ring, and said polycyclic compound residue having 7–14 carbon atoms in total, its hydrate and/or its salt.

8 Claims, 1 Drawing Sheet

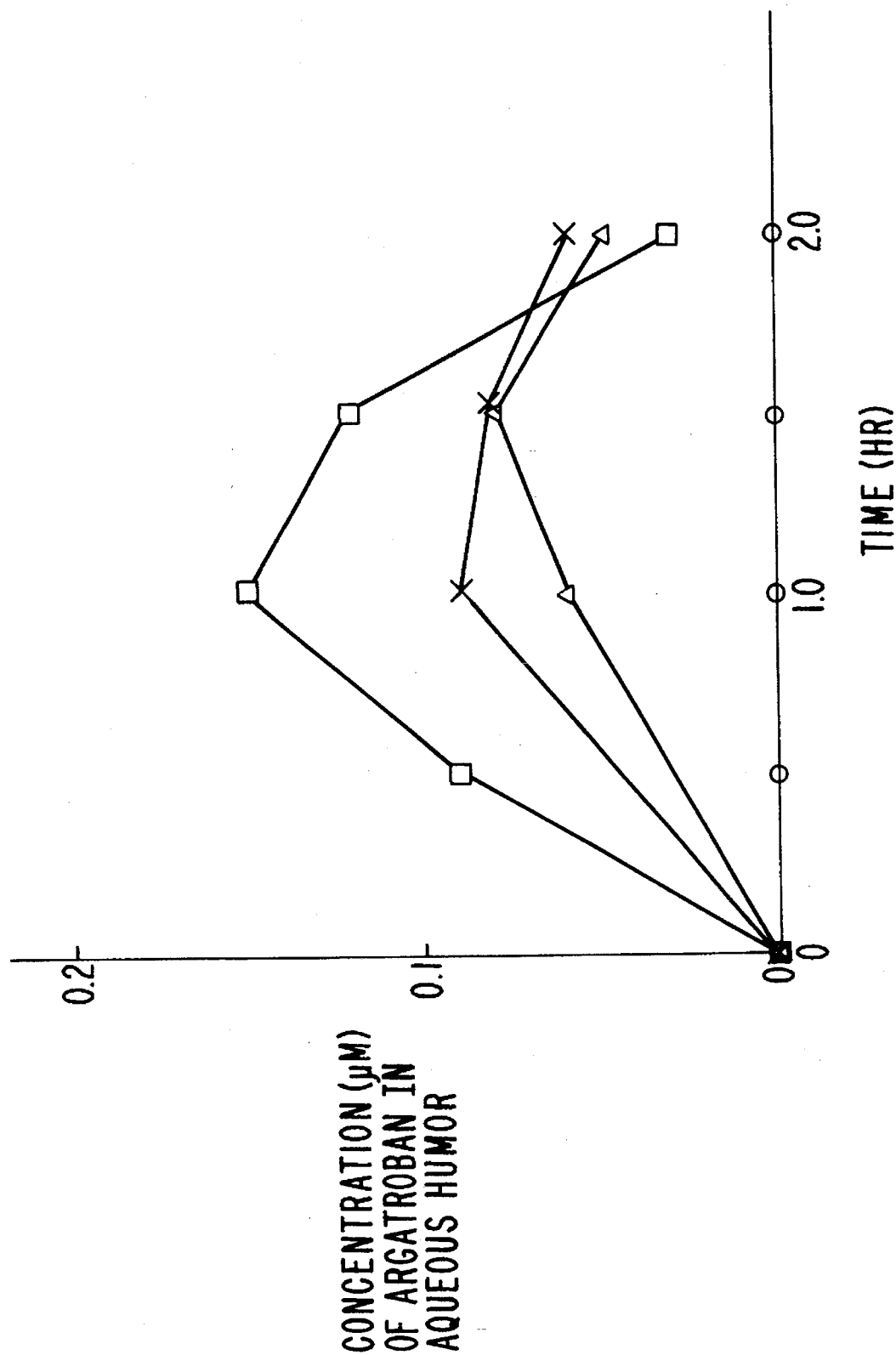

METHOD FOR INHIBITING THROMBOSIS

The present invention relates to an antithrombin composition and a process for the preparation thereof. More particularly, this invention is directed to an antithrombin composition in the form of an emulsion which comprises an arginineamide, a solvent, a diluent, and an emulsifier, and to a process for preparing the same.

Arginineamides described in Japanese Patent Application Laid-open Nos. 15267/1981, 33499/1980 and 92213/1981 are knownas being useful as an antithrombin agent, but these compounds in the form of a conventional aqueous solution show low topical absorption. For example, the permeation of these compounds through cornea cannot be detected when they are administered in the form of an eye drop.

Of known arginineamides, commercially available argatroban [(2R,4R)-1-[N²-((RS)-3-methyl-1,2,3,4-tetrahydro-8-quinolinesulfonyl)-L-arginyl]-4-methyl-2-piperidinecarboxylic acid hydrate] is a compound exhibiting selective antithrombin activity under a quite novel mechanism which has not been seen in known antithrombin agents. This compound has been used for inhibiting the formation of thrombosis generated within the blood vessel.

Since argatroban itself is hardly soluble in various pharmaceutically acceptable conventional solvents, it is usually administered in the form of an intravenous drip injection so that 10 mg/20 ml of argatroban may be administered over 2 to 3 hours twice a day. Further, for example, there has not been established any satisfactory formulation which allows the permeation of argatroban through cornea when administered in the form of an eye drop.

In such a situation as mentioned above, there has been an earnest desire to develop an administering system of antithrombin agents including argatroban, which system is applicable to all thrombin-associated conditions, except for chronic arteriosclerosis, such as postoperation of heart or blood vessel, various thrombosis diseases inclusive of cerebral thrombosis, acute cardiomuscular sclerosis, pulmonary infarction or the like, prevention of entoptic postoperative fibrin formation during the surgery of amphiblostrodes, vitreous body, cataract, glaucoma or the like diseases, inhibition of coagulation of perfusion blood during extracorporeal blood circulation and the like, where the unique actions possessed by antithrombin agents, such as the actions inhibiting ① depression of fibrin formation, ② stabilization of fibrin by activation of factor XIII, ③ platelet aggregation, due to thrombin, are highly desirable.

An object of the present invention is to establish a pharmaceutical formulation which is capable of improving the topical absorption of arginineamides inclusive of argatroban, for example, to produce such formulation as allowing permeation of arginineamides through cornea when applied in the form of an eye drop, and to develop such formulation as being applicable to previously-noted postoperative treatment, various thrombosis, thrombotic diseases, and the like, as well as postoperative treatment of entoptic operation for preventing entoptic fibrin formation.

As the result of intensive study, the present inventors have found that the topical absorption of arginineamides can be enhanced by administering said arginineamides in the form of an emulsion. This finding has permitted the development of various types of formulations for arginineamides.

Accordingly, the present invention provides an antithrombin composition in the form of an emulsion which comprises, together with a solvent, a diluent, and an emulsifier, $N^2$-arylsulfonyl-L-arginineamide represented by the general formula (I):

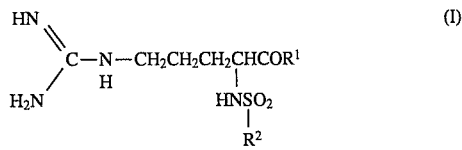

wherein $R^1$ represents (2R,4R)-4-alkyl-2-carboxypiperidino group, $R^2$ represents phenyl group or a condensed polycyclic compound residue as defined below, and said $R^2$ optionally has one or more substituents selected from lower alkyl group, lower alkoxy group or amino group substituted by lower alkyl group, said condensed polycyclic compound residue being a condensed polycyclic compound residue including a benzene ring, said benzene ring being bound to the sulfur atom of the sulfonyl group in said general formula (I), and said benzene ring being condensed with other ring which may be a heterocyclic ring, and said polycyclic compound residue having 7–14 carbon atoms in total, its hydrate and/or its salt. The present invention also provides a process for the production of the above-identified pharmaceutical composition.

The present invention will be explained in detail below.

$R^1$ in the general formula (I) represents (2R,4R)-4-alkyl-2-carboxypiperidino group, wherein "alkyl" means $C_1$–$C_5$ lower alkyl group such as methyl group, ethyl group, propyl group, isopropyl group or butyl group.

$R^2$ represents phenyl group or a condensed polycyclic compound residue as defined below.

The condensed polycyclic compound residue is a condensed polycyclic compound residue including benzene ring, said benzene ring being bound to the sulfur atom of the sulfonyl group in the general formula (I) and said benzene ring being condensed with other ring which may be a heterocyclic ring, and said polycyclic compound residue having 7–14 carbon atoms in total.

More preferably, the condensed polycyclicfunctional compound residue is a bicyclic compound residue or tricyclic compound residue. In the case of the bicyclic compound residue, the benzene ring may be preferably condensed with 5-membered ring or 6-membered ring compound, and said 5-membered ring or 6-membered ring compound may be heterocyclic compound. In the case of the tricyclic compound residue, a 5-membered ring or 6-membered ring compound may be condensed with another 5-membered ring or 6-membered ring compound, and the latter may also be heterocyclic. The hetero atom constituting such a heterocyclic compound may be oxygen atom, nitrogen atom or sulfur atom.

Further, $R^2$ may be substituted by one or more substituents selected from lower alkyl group, lower alkoxy group or amino group substituted by lower alkyl group. The lower alkyl group means $C_1$–$C_5$ alkyl group such as methyl group, ethyl group, propyl group, isopropyl group, butyl group, isobutyl group or tert-butyl group. The lower alkoxy group means $C_1$–$C_5$ alkoxy group such as methoxy group, ethoxy group, propoxy group, isopropoxy group or butoxy group. The amino group substituted by lower alkyl group includes alkylamino group and dialkylamino group substituted by said lower alkyl group.

Specific examples of the condensed polycyclic compound residue represented by $R_2$ include anthryl group, phenanthryl group, benzofuranyl group, dibenzothienyl group, phenoxazinyl group, quinolyl group, carbazolyl group, acridinyl group, phenazinyl group, phenothiazinyl group, phenoxadinyl group, benzimidazolyl group, fluorenyl group, 2,3-dihydrobenzofuranyl group, thioxanthenyl group, naphthyl group, tetrahydronaphthyl group, isoquinolyl group, tetrahydroquinolyl group, tetrahydroisoquinolyl group and the like. The benzene group of said polycyclic compound residue is bound to the sulfur atom of the sulfonyl group in the general formula (I), but the binding position on the benzene ring is not limited.

Specific examples of the compounds of the present invention are shown below.

(2R,4R)-1-[N$^2$-(3-isopropoxybenzenesulfonyl)-L-arginyl]4-methyl-2-piperidinecarboxylic acid, (2R,4R)-1-[N$^2$-(3,5-dimethyl-4-propoxybenzenesulfonyl)-L-arginyl]-4-methyl-2-piperidinecarboxylic acid, (2R,4R)-1-[N$^2$-(5,6,7,8-tetrahydro-2-naphthalenesulfonyl)-L-arginyl]-4-methyl-2-piperidinecarboxylic acid, (2R,4R)-1-[N$^2$-(5-dimethylamino-1-naphthalenesulfonyl)-L-arginyl]-4-methyl-2-piperidinecarboxylic acid, (2R,4R)-1-[N$^2$-(3-methyl-1,2,3,4-tetrahydro-8-quinolinesulfonyl)-L-arginyl]-4-methyl-2-piperidinecarboxylic acid, (2R,4R)-1-[N$^2$-(2-dibenzothiophenesulfonyl)-L-arginyl]-4-methyl-2-piperidinecarboxylic acid, (2R,4R)-1-[N$^2$-(2,4-dimethoxy-3-butoxybenzenesulfonyl)-L-arginyl]-4-methyl-2-piperidinecarboxylic acid, (2R,4R)-1-[N$^2$-(3,5-dimethyl-4-propoxybenzenesulfonyl)-L-arginyl]-4-methyl-2-piperidinecarboxylic acid, (2R,4R)-1-[N$^2$-(3-ethyl-1,2,3,4-tetrahydro-8-quinoline-sulfonyl)-L-arginyl]-4-methyl-2-piperidinecarboxylic acid, (2R,4R)-1-[N$^2$-(2-carbazolesulfonyl)-L-arginyl]-4-methyl-2-piperidinecarboxylic acid, (2R,4R)-1-[N$^2$-(2-fluorenesulfonyl)-L-arginyl]-4-methyl-2-piperidinecarboxylic acid, (2R,4R)-1-[N$^2$-(2-phenoxazinesulfonyl)-L-arginyl]-4-methyl-2-piperidinecarboxylic acid, (2R,4R)-1-[N$^2$-(2-anthracenesulfonyl)-L-arginyl]-methyl-2-piperidinecarboxylic acid, (2R,4R)-1-[N$^2$-(7-methyl-2-naphthalenesulfonyl)-L-arginyl]-4-methyl-2-piperidinecarboxylic acid, and the like. Among them, previously-noted argatroban is most preferred.

The above compounds can exist in the form of optical isomers and diastereomers, and the arginineamides of the present invention include all of them.

The arginineamides can be easily prepared according to, for example, the method as described in Japanese Patent Application Laid-open No. 15267/1981.

The arginineamides of the present invention can be converted into acid addition salts thereof with various inorganic acids or organic acids, inorganic bases or organic bases according to the method as described in Japanese Patent Application Laid-open No. 15267/1981. Moreover, their hydrates can be prepared in a conventional manner.

The solvents used in the pharmaceutical composition of the invention include unsaturated fatty acids or water/ethanol mixture.

The unsaturated fatty acids include oleic acid, linolic acid, linolenic acid and the like, but no limitation is given as far as they are pharmaceutically acceptable. The oleic acid is most preferred. Where water/ethanol mixture is used, preferable content of ethanol is 50–95%, more preferably about 90%.

As the diluents, vegetable oils or hydrocarbons may be used. The vegetable oils include soybean oil, olive oil, castor oil, sesame oil, corn oil, coconut oil, camellia oil, rape oil, peanut oil and the like. These oils can be used singly or in a combination thereof. The castor oil is preferred. As the hydrocarbons are used squalane, liquid paraffin, vaseline, or the like.

According to the process of the present invention, an arginineamide is dissolved in a solvent and diluted with a diluent so that the composition may contain 0.01–3% by weight of an arginineamide, 1–50%, preferably 1–20%, by weight of a sum of the solvent and the diluent, with respect to the total weight of the composition. Appropriate ratio of the solvent with respect to the mixture of the solvent and the diluent is 1–40%, preferably 3–30%, by weight.

No special limitation is given to the emulsifier, and the emulsifiers include soybean lecithin, hydrogenated soybean lecithin and surfactants such as polyoxyethylene hardened castor oil, polyoxyethylene sorbitan fatty acid ester, sucrose fatty acid ester, glycerin fatty acid ester, sorbitan fatty acid ester or the like. They can be used singly or in a combination thereof.

The antithrombin composition of the present invention can include, if necessary, pharmaceutically acceptable isotonic agents such as sodium chloride, glycerin or the like, pH regulators such as sodium acetate, citric acid, sodium phosphate, boric acid-borax or the like, preservatives such as p-oxybenzoic acid ester, benzalkonium chloride, benzethoniumchloride or the like, and antioxidants or stabilizers such as α-tocopherol or the like.

The antithrombin compositions of the present invention can be prepared, for example, in the manner as shown below. Thus, an emulsifier is dissolved in and mixed with an appropriate amount of water, and other ingredients such as isotonic agents, stabilizers, preservatives or the like may be added if necessary. To this mixture is added a solution of an arginineamide which has previously been dissolved in a solvent and mixed with a diluent. Then, the resultant mixture is emulsified by a conventional emulsifying equipment. The antithrombin composition in the form of an emulsion is obtained in this way.

The antithrombin composition of the present invention thus obtained allows enhanced topical absorption of an arginineamide as compared with known medicaments. For example, the composition permits detectable permeation of an arginineamide through cornea when it is administered in the form of an eye drop, and it inhibits the formation of thrombosis and fibrin, accelerates dissolution of thrombosis, or maintains and improves topical blood circulation.

The antithrombin composition of the present invention can be used in the form of an eye drop. However, the composition may also be injected intravenously, intraarterially, intramuscularly or subcutaneously. Further, it may be administered by an enteral or a parenteral formulation. The parenteral formulation includes an eye drop, an injection described above, a nasal drop, an external drug, a suppository, and the like. In any case, pharmaceutically acceptable additives such as bases, excipients or the like may be added as necessary.

The antithrombin compositions of the present invention can be used as an eye drop. However, it can also be administered in the form of other types of formulation such as injection which is applied once a day in a short time, an enteral drug, a nasal drop, an external drug, a suppository or the like. The formulations are used for the treatment after surgery, for various thrombotic diseases, for the treatment after entoptic surgery, for extracorporeal circulation, or the like.

The following detailed examples are presented by way of illustration of certain specific embodiments of the invention. The examples are representative only and should not be construed as limiting the invention in any respect.

BRIEF DESCRIPTION OF DRAWING

In the accompanying drawing, FIG. 1 shows the concentration of argatroban transported into aqueous humor when it is administered to rabbit eyes in the form of an eye drop. The symbol o represents a control sample obtained in Comparative Example 1, ¤ represents the antithrombin composition obtained in Example 2, Δ represents the antithrombin composition obtained in Example 3, and x represents the antithrombin composition obtained in Example 4.

EXAMPLE 1

In sterilized and purified water (50 ml) was dissolved polysolbate 80 (polyoxyethylene sorbitan monooleate) (5.5 g). An oily layer of a mixture comprising argatroban (1.0 g) dissolved in a mixture of oleic acid (40.0 g) and squalane (10.0 g) was added to the solution, and the resultant mixture was stirred by Silverson Mixer for micronizing the emulsion drops to give the objective antithrombin composition in the form of emulsion.

EXAMPLE 2

In sterilized and purified water (50 ml) was dissolved polysolbate 80 (0.6 g). To this solution was added an oily layer of a mixture comprising argatroban (1.0 g) dissolved in a mixture of oleic acid (40.0 g) and squalane (10.0 g), and the resultant mixture was stirred by Silverson Mixer for micronizing the emulsion drops to give the objective antithrombin composition.

EXAMPLE 3

In sterilized and purified water (95 ml) was dissolved Ryoto Sugar Ester (Sugar Ester (1670) manufactured by Mitsubishi Kasei Food Co.) (0.5 g), and then argatroban (0.18 g) was added and dissolved. An oily layer of a mixture comprising argatroban ( 0.02 g ) previously dissolved in a mixture of oleic acid (0.5 g) and castor oil (4.5 g) was added to the mixture, which was in turn subjected to micronization of the emulsion drops by means of Ultrasonicator to give the objective antithrombin composition.

EXAMPLE 4

The same procedure as in Example 3 was repeated except that water/ethanol mixture (Water: Ethanol=1:9) (0.5 ml) was used in lieu of oleic acid (0.5 g). Thus, the objective antithrombin composition was obtained.

Comparative Example 1

In sterilized and purified water (100 ml) were dissolved polysolbate 80 (2.0 g) and sodium chloride (0.9 g). To this solution was added argatroban (0.25 g), and the resultant mixture was stirred with a magnetic stirrer. The solution was adjusted to pH 7 with an appropriate amount of sodium hydroxide to give a comparative antithrombin composition.

Experiment 1

The antithrombin compositions obtained in Examples 2, 3 and 4 and the composition of Comparative Example 1 were administered in the form of eye drops to NZW male rabbits (body weight about 3 kg), and after the administration, the concentration of argatroban transported to aqueous humor was measured repeatedly with the lapse of time. FIG. 1 shows the result.

The above experiment revealed that the antithrombin composition prepared according to the present invention significantly accelerates the permeation of argatroban through cornea in comparison with the aqueous solution of argatroban, for example, when the compositions are administered in the form of an eye drop.

What is claimed is:

1. A method for inhibiting the formation of thrombosis and fibrin, accelerating dissolution of thrombosis or maintaining and improving topical blood circulation which comprises topically administering to a patient in need of such treatment an antithrombin composition in the form of an emulsion which comprises a solvent selected from the group consisting of an unsaturated fatty acid and a water/ethanol mixture, a diluent, an emulsifier, and an effective amount of an $N^2$-arylsulfonyl-L-arginineamide represented by the following general formula (I):

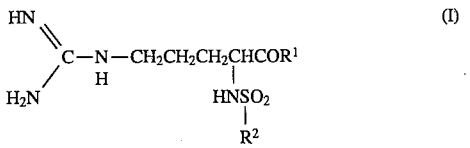

a hydrate and/or a pharmaceutically acceptable salt thereof, wherein $R^1$ represents (2R,4R)-4-alkyl-2-carboxypiperidino group, $R^2$ represents phenyl group or a condensed polycyclic compound residue as defined below, and said $R^2$ optionally has one or more substituents selected from lower alkyl group, lower alkoxy group or amino group substituted by lower alkyl group, said condensed polycyclic compound residue being a condensed polycyclic compound residue including a benzene ring, said benzene ring being bound to the sulfur atom of the sulfonyl group in the general formula (I) and said benzene ring being condensed with other ring which may be a heterocyclic ring, and said polycyclic compound residue having 7–14 carbon atoms in total.

2. A method according to claim 1, in which $R^1$ is (2R, 4R)-4-methyl-2-carboxypiperidino group and $R^2$ is 3-methyl-1,2,3,4-tetrahydro-8-quinolyl group.

3. A method according to claim 1 or 2, in which said solvent is oleic acid or water/ethanol mixture.

4. A method according to claim 1 or 2, in which said diluent is a vegetable oil or hydrocarbon.

5. A method according to claim 1 or 2, in which said diluent is castor oil or squalane.

6. A method according to claim 1, wherein said topical site is cornea.

7. A method according to claim 1 wherein the composition is in the form of an enteral or parenteral formulation.

8. A method according to claim 1 wherein the composition is administrable as an eye drop.

* * * * *